United States Patent [19]
Whitcomb

[11] Patent Number: 6,011,049
[45] Date of Patent: Jan. 4, 2000

[54] COMBINATIONS FOR DIABETES

[75] Inventor: Randall Wayne Whitcomb, Ann Arbor, Mich.

[73] Assignee: Warner-Lambert Company, Morris Plains, N.J.

[21] Appl. No.: 09/189,132

[22] Filed: Nov. 9, 1998

Related U.S. Application Data

[63] Continuation-in-part of application No. 08/970,057, Nov. 13, 1997, Pat. No. 5,859,037
[60] Provisional application No. 60/038,224, Feb. 19, 1997.

[51] Int. Cl.[7] .................. A61K 31/44; A61K 31/425; A61K 31/175; A61K 31/155
[52] U.S. Cl. .................. 514/369; 514/342; 514/593; 514/635; 514/866
[58] Field of Search .................. 514/342, 369, 514/593, 635, 866

[56] References Cited

FOREIGN PATENT DOCUMENTS

| | | |
|---|---|---|
| 0749751 | 12/1996 | European Pat. Off. . |
| 0753298 | 1/1997 | European Pat. Off. . |
| 9609823 | 4/1996 | WIPO . |

OTHER PUBLICATIONS

PCT International Search Report, PCT/US97/21996.
Oakes, et al., *Diabetes*, vol. 13:1203, 1994, A New Antidiabetic Agent, BRL 49653, Reduces Lipid Availability and Improves Insulin Action and Glucoregulation in the Rat.
Hulin, et al, *Current Pharmaceutical Design* 2:85–102, 1996, The Glitazone Family of Antidiabetic Agents.
Groop, M.D., *Diabetes Care*, 15:737–754, 1992, Sulfonylureas in NIDDM.
Nakano, et al., *CS–045*, Clinical Evaluation of a New Oral Hypoglycemic Drug, CS–045, on Daily Profile of Blood Glucose in Patients with Non–Insulin Dependent Diabetes Mellitus (1993).
*Company News On–Call*, 1–3, 1997 Rezulin® (troglitazone) Receives FDA Marketing Clearance for use as Either Initial or Combination Therapy for Type 2 Diabetes.
Spencer, et al., *Drugs*, vol. 54:89–101, 1997, Troglitazone.
Yamasaki, et al., *The Tokohu Journal of Experimental Medicine*, vol. 183:173–183, 1997, Pioglitazone (AD–4833) Ameliorates Insulin Resistance in Patients with NIDDM.
Iwamoto, et al., *Diabetic Medicine*, vol. 13:365–370, 1996, Effect of Combination Therapy of Troglitazone and Sulphonylureas in Patients with Type 2 Diabetes Who Were Poorly Controlled by Sulphonylurea Alon.
Bressler & Johnson., *Drugs& Aging*, vol. 9:418–437, 1996, Oral Antidiabetic Drug Use in the Elderly.
Okaka, et al., *Chemical Abstracts*, vol. 126, No. 20, 1997, Abstract No. 258925, Antidiabetic Effects of Pioglitzone HCl Alone or in Combination with Insulin or Sylfonylurea in Diabetic Animals.
De Souza, et al., *Diabetes*, vol. 44:984–991, 1995, Insulin Secretory Defect in Zucker fa/fa Ratsis Improved by Ameliorating Insulin Resistance.

*Primary Examiner*—Kimberly Jordan
*Attorney, Agent, or Firm*—Charles W. Ashbrook

[57] ABSTRACT

Combinations of a glitazone antidiabetic agent and a biguanide antidiabetic agent, and optionally a sulfonylurea antidiabetic agent, are useful for treating diabetes mellitus and improving glycemic control.

16 Claims, 12 Drawing Sheets

COMBINATIONS FOR DIABETES

CROSS-REFERENCE TO RELATED APPLICATION

This is a continuation-in-part of Ser. No. 08/970,057, filed Nov. 13, 1997, now U.S. Pat. No. 5,859,037, which claimed priority to U.S. provisional Ser. No. 60/038,224, filed Feb. 19, 1997.

FIELD OF THE INVENTION

This invention relates to combinations of antidiabetic compounds, and to a method for treating diabetes employing such combinations.

BACKGROUND OF THE INVENTION

Diabetes mellitus is a metabolic disorder characterized by hyperglycemia, insulin resistance, and is often associated with other disorders such as obesity, hypertension, hyperlipidemia, as well as complications such as cardiovascular disease, retinopathy, neuropathy, and nephropathy. The disease is progressive in nature, and can often be controlled initially by diet alone, but generally requires treatment with drugs such as sulfonylureas and injections of exogenous insulin. A new class of compounds known as the glitazones has recently received a great deal of attention for their ability to treat diabetes. These compounds operate by increasing the sensitivity of insulin receptors throughout the body, thereby diminishing or eliminating the need for exogenous insulin. Another agent known as a biguanide also is used to decrease hepatic glucose production as well as intestinal absorption of glucose.

It has now been discovered that combination therapy with a biguanide and a glitazone results in dramatic improvement in glycemic control, and that even better control can be achieved by using a combination comprised of a biguanide, a glitazone, and a sulfonylurea. Accordingly, such combinations are especially useful in treating diabetes and associated complications.

SUMMARY OF THE INVENTION

This invention provides a method of treating diabetes by administering to a subject in need of treatment a combination of a sulfonylurea antidiabetic agent and an antidiabetic glitazone, together with a biguanide antidiabetic agent such as metformin, or simply a glitazone together with a biguanide. The clinical data presented herein establishes the unexpected biological benefits achievable with these combinations.

The sulfonylureas are a class of compounds that have been widely employed to treat diabetes. Such compounds are well known, for example as described in U.S. Pat. Nos. 3,454,635, 3,669,966, 2,968,158, 3,501,495, 3,708,486, 3,668,215, 3,654,357, and 3,097,242. Most of the sulfonylurea antidiabetics are defined by the formula

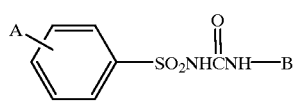

where A is hydrogen, halo, or an organic radical such as alkyl, alkanoyl, aryl, aralkyl, heteroaryl, and cycloalkyl, and B is alkyl, cycloalkyl, and a heterocyclic group such as hexahydroazepine. Preferred sulfonylureas to be employed are those wherein A is chloro, alkyl such as methyl, or alkyl substituted with aryl carbonyl or aryl carboxamido, for instance 3-chloro-5-methoxybenzoylethyl or 5-methyl-2-pyrazinylcarbonylaminoethyl.

Especially preferred sulfonylureas to be employed in the combinations of this invention are glyburide, gliquidone, glipizide, tolbutamide, tolazamide, glisoxepid, chlorpropamide, glibornuride, gliclazide, glimepiride, phenbutamide, and tolcyclamide.

According to this invention, the foregoing sulfonylureas are used in combination with a glitazone to treat diabetes and to improve glycemic control. The glitazones are a family of antidiabetic agents characterized as being thiazolidinediones or related analogs. They are described in *Current Pharmaceutical Design*, 1996;2:85–101. Typical glitazones have the formula

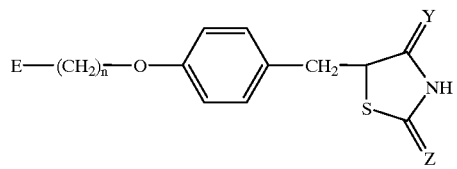

where n is 1, 2, or 3, Y and Z independently are O or NH; and E is a cyclic or bicyclic aromatic or non-aromatic ring, optionally containing a heteroatom selected from oxygen or nitrogen.

Preferred glitazones have the formula

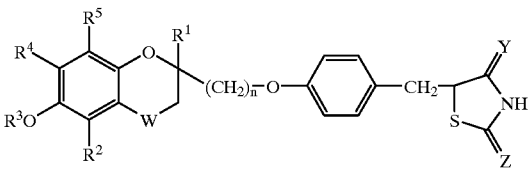

wherein:
  $R^1$ and $R^2$ independently are hydrogen or $C_1$–$C_5$ alkyl;
  $R^3$ is hydrogen, a $C_1$–$C_6$ aliphatic acyl group, an alicyclic acyl group, an aromatic acyl group, a heterocyclic acyl group, an araliphatic acyl group, a ($C_1$–$C_6$ alkoxy) carbonyl group, or an aralkyloxycarbonyl group;
  $R^4$ and $R^5$ independently are hydrogen, $C_1$–$C_5$ alkyl, $C_1$–$C_5$ alkoxy, or $R^4$ and $R^5$ together are $C_1$–$C_4$ alkylenedioxy;
  W is —$CH_2$—, >CO, or CHOR$^6$, where $R^6$ is any one of the atoms or groups defined for $R^3$ and may be the same as or different from $R^3$;
  n, Y, and Z are as defined above, and pharmaceutically acceptable salts thereof.

An especially preferred glitazone is troglitazone having the formula

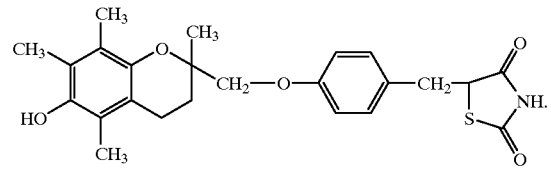

Other glitazones that can be employed in this invention are described in U.S. Pat. No. 5,457,109, which is incorporated herein by reference. Other specific glitazones which are preferred include ciglitazone, pioglitazone, englitazone, TA 174, which has the formula

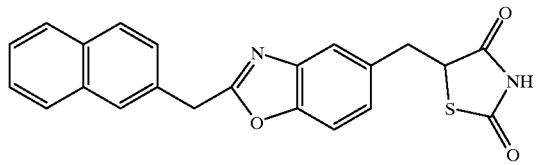

and BRL 49653, which has the formula

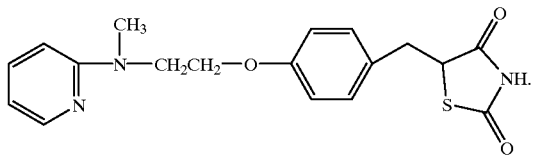

Additionally preferred glitazones include:
5-(4-[2-[1-(4-2'-Pyridylphenyl) ethylideneaminooxy] ethoxy]benzyl]-thiazolidine-2,4-dione;
5-(4-[5-Methoxy-3-methylimidazo[5,4-b]pyridin-2-yl-methoxy) benzyl]-thiazolidine-2,4-dione, or its hydrochloride;
5-[4-(6-Methoxy-1-methylbenzimidazol-2-yl-methoxy) benzyl]-thiazolidine-2,4-dione;
5-[4-(1-Methylbenzimidazol-2-ylmethoxy) benzyl] thiazolidine-2,4-dione; and
5-[4-(5-Hydroxy-1,4,6,7-tetramethylbenzimidazol-2-ylmethoxy) benzyl]-thiazolidine-2,4-dione.

A typical biguanide is metformin. It typically is used clinically as a pharmaceutically acceptable salt, preferably the hydrochloride salt. A commercial form of metformin hydrochloride is available, and its chemical name is N,N-dimethylimidodicarbonimidic diamide hydrochloride. Metformin hydrochloride has the structural formula

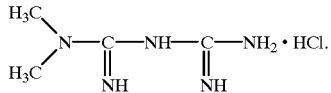

As used herein, "metformin" means the base compound as well as its pharmaceutically acceptable salts. Metformin is used clinically to manage NIDDM, particularly in patients who are not effectively treated with a sulfonylurea. While it is not chemically related to the sulfonylureas, it routinely is utilized in combination with a sulfonylurea, and has been shown to be synergistic in some cases. Other biguanides can also be used.

DETAILED DESCRIPTION OF THE INVENTION

Figure 1:
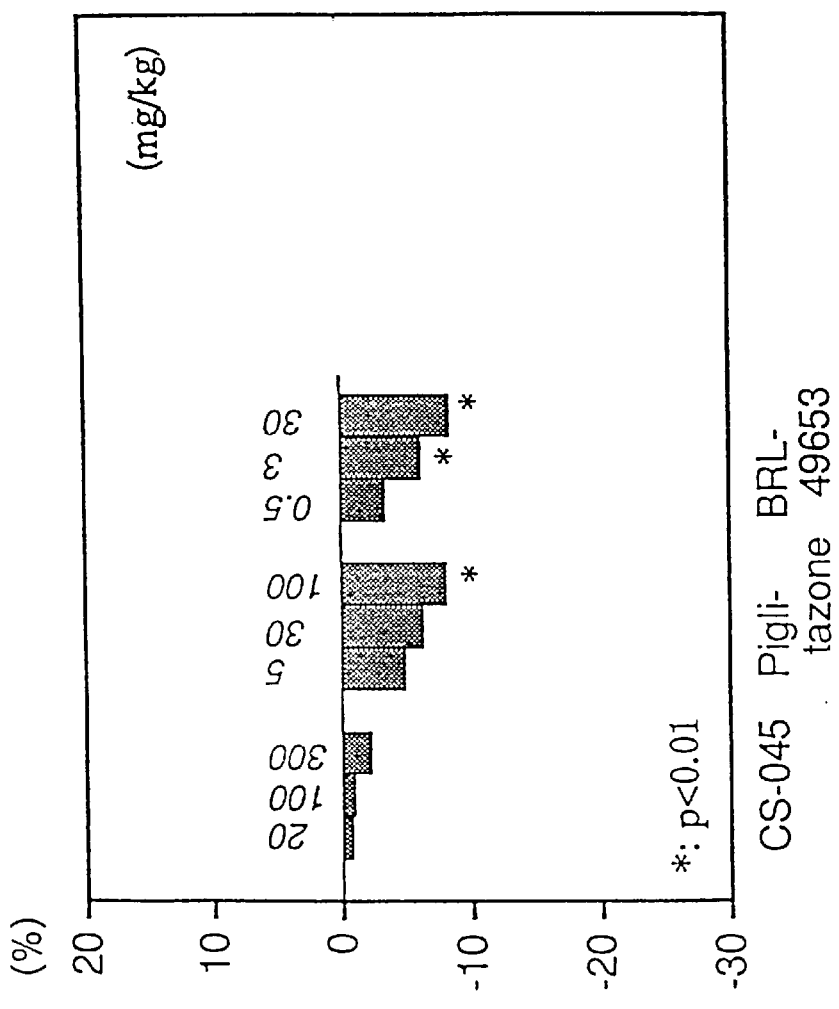
FIG. 1 Dose response of CS-045 (troglitazone), pioglitazone, and BRL-49653 (rosiglitazone) in causing reduction in red blood cell counts in female rats.

According to this invention, a glitazone is used in combination with a biguanide, or in combination with both a sulfonylurea and a biguanide, to treat diabetes and to improve glycemic control in patients in need of treatment. The compounds can be employed individually, or can be combined in a single formulation, for example as a tablet, capsule, syrup, solution, as well as controlled release formulations. In a preferred embodiment, the sulfonylurea, biguanide, and glitazone are formulated individually and administered in the same manner that each is normally used clinically.

The dosage of each agent will vary depending upon the severity of the disease, the frequency of administration, the particular agents and combinations utilized, and other factors routinely considered by an attending medical practitioner. The sulfonylurea normally will be administered at a daily dose of from about 0.25 mg to about 500 mg, typically about 3 mg to about 250 mg. A typical dosage for glyburide, for example, will be about 10 to about 20 mg per day. The glitazones will normally be administered at doses from about 5 mg to about 2500 mg per day, and more typically from about 50 mg to about 1500 mg per day. A preferred glitazone is troglitazone, and it will be employed at doses from about 100 mg to about 1000 mg per day. A further preferred glitazone is rosiglitazone (BRL 49653), and it will be employed at doses of about 5 mg to about 10 mg per day. Another preferred glitazone is pioglitazone, and it will be employed at doses of about 50 mg to about 200 mg per day. Metformin hydrochloride will be administered at doses of about 300 mg to about 2000 mg per day. It is available commercially in tablets which contain 500 mg and 850 mg of active agent. These can be given up to two times a day or more.

Typical combinations to be employed according to this invention thus include troglitazone plus metformin, and troglitazone plus metformin plus a sulfonylurea such as glyburide. Another typical and preferred combination is rosiglitazone plus metformin, and rosiglitazone plus metformin plus a ;sulfonylurea such as glyburide. Still another preferred combination is pioglitazone plus metformin, and pioglitazone plus metformin plus a sulfonylurea such as glyburide. These combinations produce better than expected control of NIDDM.

The invention provides compositions of antidiabetic agents, for example, metformin and a glitazone, as well as metformin, a sulfonylurea and a glitazone, and a method of treating diabetes and controlling glycemic conditions comprising administering to a patient in need of treatment an effective amount of metformin and a glitazone, or metformin, a sulfonylurea and an effective amount of a glitazone. When the sulfonylurea and glitazone are formulated together, the compositions will contain about one to about 1000 parts by weight of sulfonylurea, and about 1000 to about one part by weight glitazone. For example, a typical composition of glyburide and troglitazone will contain about 12 mg of glyburide and about 500 mg of troglitazone. Such combination will be administered to an adult patient about once each day to achieve a desired glycemic control. Metformin can be combined directly with a glitazone such as troglitazone. Typical doses will be about 500 mg of metformin and about 300 to 600 mg of troglitazone. A typical three-way composition includes 12 mg of glyburide, 400 mg of troglitazone, and 500 mg of metformin.

The compositions may contain common excipients and carriers such as starch, sucrose, talc, gelatin, methylcellulose, and magnesium stearate. The compositions will normally be made for oral administration, for instance as tablets or capsules, but also may be in the form of aqueous suspensions or solutions, suppositories, slow release forms, for example employing an osmotic pump, skin patch, or the like.

The method of treating diabetes employing a combination provided by this invention has been established in a long-term controlled clinical evaluation. A typical study determined the efficacy and safety of troglitazone alone and in combination with the sulfonylurea glyburide for the treatment of non-insulin dependent diabetes mellitus (NIDDM). This study targeted the segment of the NIDDM population in which the disease state has progressed to a point where maximum doses of sulfonylureas no longer produce adequate glycemic control. These patients are at a stage where the maximally stimulated pancreatic insulin secretion does not keep up with the increasing demand. Since the unstimulated (absence of sulfonylurea) insulin secretory capacity of the beta cells is very low in this population, reversing insulin resistance alone would be of partial benefit. Therefore, maintaining a level of stimulated insulin secretion with a sulfonylurea while adding troglitazone to improve insulin sensitivity could provide a level of glycemic control unattainable by either medication alone.

A primary objective of the study was to assess the efficacy of troglitazone alone or in combination with micronized glyburide in patients with NIDDM by comparing changes in markers of glycemic and lipid homeostasis over 1 year of treatment. Long-term safety was also an objective of this study, assessed by adverse events and clinical laboratory data.

The effect of treatment on the pattern of post-prandial glucose tolerance (standard 2-hour meal tolerance test) was determined in a subset of patients. In addition, heart mass and function (echocardiographic procedure) were monitored in a subset of patients.

Based upon this study, the U.S. Food and Drug Administration has now approved the use of troglitazone in combination with sulfonylureas in the treatment of type II diabetes. Troglitazone is now routinely used clinically in combination with sulfonylureas, especially glyburide. A brief summary of the results of the 12-month, 30-center clinical trial study in 552 patients is presented below.

Overview

Troglitazone monotherapy and troglitazone/glyburide combination therapy were well-tolerated throughout the study. Overall, 70% of patients treated with troglitazone monotherapy had adverse events compared with 90% of patients treated with glyburide (control) therapy. Patients treated with combination therapy had an incidence of adverse events similar to glyburide therapy, 91%. To what extent the high dropout rate for troglitazone monotherapy affected the incidence of adverse events is not known.

In general, the incidence of adverse events was not influenced by age or menopausal status. Overall, patients treated with combination therapy had a higher incidence of associated adverse events (26%) compared with those treated with glyburide (10%).

The incidence of serious adverse events was similar across all treatments; the percent of patients withdrawn for adverse events was 8% across treatments.

Clinical Laboratory Measurements

Changes From Baseline to Outside Normal Range

Baseline clinical laboratory parameters were compared with values at the end of the study (last visit) to identify any abnormal trends. The percent of patients with increases or decreases in laboratory values were calculated based on the number of patients at risk for changes outside of the reference range; i.e., patients with low or high values at baseline were not considered at risk for a decrease or increase, respectively.

No clinically adverse trends were noted in any laboratory parameter. However, dramatic improvement (i.e., decreases) in urine glucose for all combination therapy groups was evident.

Clinically Important Changes

The Guidelines for Evaluation of Clinical Laboratory Values were used to identify those patients that may have had a clinically important change in one or more laboratory values at any point during the study. Laboratory results were then reviewed for these particular patients to determine which patients actually had clinically important changes in a given laboratory parameter. Minimal changes occurred within any laboratory parameter across all treatments.

Patients meeting criteria for clinically important changes are discussed below. A greater number of patients treated with troglitazone combination therapy than troglitazone monotherapy had laboratory changes meeting clinically meaningful change criteria. One patient had significantly elevated ALT and AST which was considered attributable to study drug by the investigator and which causality cannot be confidently ruled out: Patient 4, Center 16, experienced significantly elevated ALT (1155 U/L) and AST (458 U/L) following 57 days of troglitazone 600 mg combination therapy and receiving a flu vaccine. ALT and AST returned to baseline levels 49 days after therapy was withdrawn.

Specific Laboratory Parameters

Hematology: Minimal changes occurred with any of the hematological parameters. Changes that met criteria for possible clinical importance were increases or decreases within the normal range or transient changes that subsequently resolved. Patients meeting clinically important changes in hematology parameters are noted here. Thirty-four patients had changes in hemoglobin or hematocrit or both meeting criteria for clinically meaningful change. Seven patients had mildly transient decreases which returned to baseline levels while remaining on troglitazone (3 patients; two on 400 mg, one on 600 mg) or troglitazone combination (4 patients; three on 400 mg/12 mg, one on 600 mg/12 mg). Eight patients had slight decreases within the normal range or were near the lower normal limit at baseline and dropped below normal limits during the study, and hemoglobin or hematocrit levels remained stable throughout the study. Eight patients had levels below normal reference limits for hemoglobin or hematocrit at baseline and remained below normal limits throughout the study, none were withdrawn for this reason. Fourteen patients had decreases in hemoglobin and hematocrit secondary to blood loss for several reasons, e.g., acute bleeding due to automobile accident, rectal bleeding due to hemorrhoids, donated blood, bleeding ulcer (2 patients), CABG surgery (4 patients). Two of these patients were consuming up to 50 concurrent medications and two additional patients had severe infections associated temporally with decreased hemoglobin and hematocrit. After thorough review of patient laboratory data, no patient experienced clinically important decreases in any hematological parameter that can be directly attributable to troglitazone.

Liver Enzymes: Thirteen patients had clinically meaningful elevations in ALT, AST, or both. Three of these patients were terminated due to enzymes elevations; all were followed and enzymes returned to either baseline or within normal limits. Four additional patients had transient elevations which resolved while remaining on troglitazone or troglitazone combination. Two patients on troglitazone 600 mg combination, three on troglitazone 300 mg combination, and one patient on troglitazone 200 mg monotherapy had mildly elevated (<3×upper normal limit) at the end of the study. Three of these patients were concomitantly using many additional medications for concurrent illness which cannot be ruled out as causal or contributory to their elevated enzymes.

DISCUSSION

Although troglitazone enhances insulin action at the cellular level, it does not stimulate insulin release nor does it mimic its action. The therapeutic benefits of troglitazone treatment depend on the availability of adequate amounts of insulin. The addition of troglitazone to concurrent sulfonylurea treatment provides a balance of stimulated release of insulin while ameliorating insulin resistance. The results obtained in this study support this hypothesis and provide evidence of significant improvement in glycemic control of patients with very few remaining therapeutic options.

Glycemic Parameters

The mean change from baseline in FSG for the 600T/12G arm was −56 mg/dL, representing a difference of −79 mg/dL from the control arm. The improvement in FSG is confirmed by a mean change from baseline in $HbA_{1c}$ of −1.75% in the same treatment arm, a difference of −2.65% from the active control arm. Approximately 60% of patients in the 600 T/12 g arm reached an $HbA_{1c}$ level ≦8%. The magnitude of these changes represent an impressive improvement in glycemic control without the use of exogenous insulin. Although the glycemic improvements observed in the 400T/12G and the 200T/12G arms were less pronounced, these data provide the rationale for titration based on the level of glycemic control.

The results of the troglitazone monotherapy treatment arms, on the other hand, should be interpreted carefully. Considering the slow acting properties of troglitazone, an immediate switch from sulfonylurea to troglitazone would cause a deterioration in glycemic control before any improvement is observed. Moreover, the immediate switch in patients who are already in poor control would worsen the degree of glucose toxicity and make adequate glycemic control even harder to achieve. This situation was observed in the monotherapy arms. Those patients were switched from the maximum dose of glyburide to troglitazone monotherapy at the time of randomization. Consequently, glycemic control in the majority of patients worsened, and patients with excessive hyperglycemia were withdrawn from the study for safety purposes. Due to the nature of the ITT analysis with LOCF, the average change in FSG and $HbA_{1c}$ is reflective of the high glycemic values of patients who discontinued early. In other words, the higher the early dropout rate, the worse the end of study results would appear. This is especially the case in the T200 arm since the dropout rate due to lack of efficacy reached almost 60%. Therefore, the results of the ITT analysis in this case are not a good reflection of the true response of all patients. On the other hand, the results of the completers analysis represent a bias in favor of troglitazone. The completers analysis would effectively select the sub-population who are more likely to respond to study medication. The true response of these treatment arms is more likely to lie somewhere between the results of the ITT and completers populations. Nevertheless, the clinical interpretation of these data indicates that switching patients from sulfonylurea use, particularly those on high doses, to troglitazone monotherapy is not an appropriate therapeutic approach.

Troglitazone should be added to current treatment regimens of a sulfonylurea beginning at 200 mg and increasing up to 600 mg as needed to optimize glycemic control. As patients reach target goals of glycemic control, the dose of sulfonylurea may be reduced or even eliminated based on the level of glycemic control. Hence, in these patients (sulfonylurea failures), troglitazone as monotherapy is achieved only if warranted based upon glycemic control parameters. Faced with the alternative of reducing the dosage of one of the agents, the pathophysiology of the disease should be considered. Treating the basic defect of type II diabetes, i.e., insulin resistance, should take precedence over exhausting pancreatic insulin secretion by sulfonylurea stimulation. Therefore, as glycemic control improves the sulfonylurea should be considered for dose reduction or even discontinuation if indicated. Troglitazone alone can be effective in naive patients who are not well-controlled on diet and exercise but have not been managed on oral agents. The deficit in the insulin secretory capacity of naive patients is generally relative, and the improvement in insulin sensitivity may be sufficient to restore normoglycemia.

Insulin, C-peptide, and Meal Tolerance Test

The insulin reduction observed in the combination treatment arms reflects an improvement in insulin sensitivity since the lower insulin level is associated with significant decreases in FSG and $HbA_{1c}$ rather than increases. The direction of the change in the fasting levels of insulin and serum glucose is mirrored by similar changes in the AUC of the insulin and serum glucose during the meal tolerance test for the combination arms. The improved insulin sensitivity leads to a reduced demand on pancreatic secretion of insulin, a desirable outcome given the natural progression of the disease.

The magnitude of the reduction in insulin in the monotherapy arms is greater than that observed in the various combination arms. While a similar reduction between the monotherapy and the combination treatment arms would have been expected based upon enhanced insulin activity, the additional decrease in insulin levels may be attributed to the removal of sulfonylurea-stimulated insulin secretion. Finally, the reduction observed in the control arm (micronized glyburide) may be attributed to gradual degradation of the pancreatic secretory function or secondary failure typically observed with sulfonylurea treatment over time. This change cannot be attributed to improvements in insulin sensitivity, since FSG levels increased and did not decrease. The observed changes in insulin levels were confirmed by similar changes in direction and magnitude in C-peptide levels for all treatment arms.

Lipid Parameters

The classical manifestations of insulin resistance in a diabetic population are elevated triglycerides and low levels of HDL. Therefore, the reversal of insulin resistance should be expected to elicit favorable changes in these lipid parameters, as observed in this study. Although statistical significance was reached in some (but not all) treatment arms, the general trend of the changes is consistent with the reversal of insulin resistance, i.e., a reduction in triglycerides and an increase in HDL. The reduction in insulin levels and resultant increase in lipoprotein lipase (LPL) activity could be responsible for the triglyceride and HDL changes. Modest increases of minimal clinical significance in total cholesterol and LDL were observed in the monotherapy arms. Similar, but less pronounced changes were observed in the combination arms. It is important to note that LDL levels were measured directly and not calculated indirectly from triglycerides and cholesterol levels using the Freidwald formula. Both LDL and cholesterol are relatively constant parameters and are not affected by the fasting state of the patient. Triglycerides, however, are extremely variable, and affected by the fasting state of the patient. This variability could explain the fact that a clinically desirable mean reduction in excess of 50 mg/dL observed in the T600/G 12 group did not reach statistical significance. In contrast, the magnitude of change in both cholesterol and LDL was of little clinical significance (only 4%–7% in the combination treatment arms) but was statistically significant.

Lipid changes observed in this study are consistent with results from prior studies. The favorable change in triglycerides, HDL, and FFA are contrasted by minimal increases in total cholesterol, LDL, Lp(a), and no changes in Apo (A1) and Apo (B). Collectively, these changes may be interpreted as having a potentially beneficial impact on atherogenic risk. It should be noted that patients with elevated triglycerides levels could potentially benefit from troglitazone treatment and provide synergism to the management of their dyslipidemia since elevated triglyceride levels are recognized as an independent risk factor for cardiovascular disease.

Blood Pressure

No statistically or clinically significant changes were observed in systolic blood pressure at the end of the study. Mean diastolic blood pressure, however, decreased significantly ($p<0.05$) for patients treated with 600 mg/12 mg combination therapy. A reduction in diastolic BP is consistent with similar observation in other troglitazone studies. The direction and magnitude of the DBP change offers a clinically desirable endpoint in this population. Given the fact that hypertensive patients were excluded from this study, only minor changes would be expected. Since this study was not powered to detect small changes in blood pressure, the direction of the observed change still represents a desirable change in this population. The reduction in diastolic BP is corroborated by a decrease in the calculated peripheral resistance in the subgroup of patients that underwent cardiac output measurements in this study. This change in BP could result indirectly from reversing insulin resistance and amelioration of hyperinsulinemia, or alternatively, from a direct action of troglitazone on peripheral vasculature.

Weight

A statistically significant increase in weight was observed in the combination arms in contrast to the troglitazone monotherapy arms in which modest weight losses of 1 to 7 lbs were seen. While the magnitude of the change is relatively small (approximately 6%), minor increases in weight in this population should be carefully monitored. The fact that weight increases were observed in the combination therapy arms only and not the monotherapy arms is suggestive of factors other than troglitazone therapy being responsible for weight increases. Several factors may have contributed to weight gain in this study. The fact that weight gain was mainly observed in treatment arms associated with improved glycemic control suggests that diminished glycosuria may be contributing to weight gain. The weight increase may possibly be a result of potentiation of the known affect of sulfonylurea therapy on weight gain. In addition, patients in this study were instructed on a weight maintenance diet for the duration of the study. Appropriate diabetic diet instructions targeting ideal body weight was not implemented in this study. Finally, improving hyperglycemia and achieving target glycemic control in this population is a disincentive to maintain strict caloric and sugar intake. In clinical practice, diet and exercise should be strongly emphasized to avoid potential weight gain.

Safety

Troglitazone, both as mono- and combination therapy, was well-tolerated during the study. The overall adverse event profile of troglitazone/glyburide combination therapy was similar to the adverse event profile of glyburide monotherapy. Most adverse events occurred at the lower incidence in patients treated with troglitazone monotherapy compared with the patients treated with glyburide monotherapy. This may be attributed to a better adverse event profile for troglitazone and may in part be due to the high dropout rate for patients treated with troglitazone monotherapy. Tolerance was also evident by the rare occurrence of unacceptable levels of clinical laboratory parameters; most of these occurrences resolved while study treatment continued.

Summary

In summary, patients with type II diabetes receiving maximum doses of sulfonylurea have very few oral therapeutic options remaining. Aside from insulin resistance, the hallmark of the disease at this stage is mainly a diminished pancreatic response to glucose stimulus. Improving insulin resistance is of great benefit when added to a current regimen capable of stimulating insulin release (e.g., sulfonylurea). Combination therapy of troglitazone and sulfonylurea appears to be safe and well-tolerated and can result in significant improvement in glycemic control. It should be noted that patients on maximum doses of a sulfonylurea should not be switched to troglitazone monotherapy. Monotherapy should only be achieved if indicated by downward titration of the sulfonylurea dose. Finally, application of the results of this study should not be limited to patients who fail on maximum doses of sulfonylurea therapy but also extended to patients on lower doses of a sulfonylurea.

CONCLUSIONS

Troglitazone/glyburide combination therapy is well-tolerated and significantly (p<0.0001) improves glycemic control over a 52-week period at doses of 200 mg/12 mg to 600 mg/12 mg compared with glyburide monotherapy in patients with NIDDM who are not adequately controlled on sulfonylurea therapy.

Another glitazone, namely BRL 49653 (now known as rosiglitazone, "RSG"), has undergone clinical evaluation and has demonstrated good efficacy in controlling glycemia in patients with type II diabetes. Rosiglitazone was evaluated in a multi-center, placebo-controlled trial. In this study, 493 patients with a fasting glucose between 7.8 mmol/L and 16.7 mmol/L were randomly assigned to treatment with placebo or rosiglitazone given at 4 mg or 8 mg per day. The rosiglitazone was administered as a twice-daily regimen for 26 weeks, following a 4-week placebo run-in period. The baseline demographic and metabolic characteristics of the patient population is given in Table 1.

TABLE 1

Baseline Demographic and Metabolic Characteristics

| Baseline Characteristics, n (%) | Treatment Group | | |
|---|---|---|---|
| | Placebo (n = 158) | RSG 4 mg/day (n = 166) | RSG 8 mg/day (n = 169) |
| Age (years) | | | |
| Mean ± SD | 58.8 ± 10.9 | 59.6 ± 9.8 | 60.7 ± 9.5 |
| Range | 36–81 | 39–79 | 38–80 |
| Sex | | | |
| Males | 104 | 107 | 113 |
| Females | 54 | 59 | 56 |
| Duration of Diabetes (years) | | | |
| Mean | 4.6 | 4.8 | 5.4 |
| Previous Therapy | | | |
| Diet only | 45 | 44 | 45 |
| Previous oral agents | 113 | 122 | 124 |
| FPG[a] (mmol/L) | | | |
| Mean ± SD | 12.7 ± 3.3 | 12.6 ± 3.4 | 12.2 ± 3.5 |
| Range | 6.44–20.76 | 5.61–23.59 | 5.61–21.54 |
| $HbA_{1c}$[b] (%) | | | |
| Mean ± SD | 9.0 ± 1.66 | 9.0 ± 1.52 | 8.8 ± 1.56 |
| Range | 5.2–13.3 | 5.9–13.9 | 5.9–13.0 |
| C-Peptide[c] (mmol/L) | | | |
| Mean ± SD | 1.00 ± 0.42 | 1.02 ± 0.43 | 0.99 ± 0.47 |
| Range | 0.26–2.71 | 0.23–2.34 | 0.3–2.90 |

TABLE 1-continued

Baseline Demographic and Metabolic Characteristics

| Baseline Characteristics, n (%) | Treatment Group | | |
|---|---|---|---|
| | Placebo (n = 158) | RSG 4 mg/day (n = 166) | RSG 8 mg/day (n = 169) |
| BMI (kg/m²) | | | |
| Mean ± SD | 29.9 ± 4.13 | 30.2 ± 4.10 | 29.1 ± 3.85 |
| Range | 21.2–38.2 | 19.2–39.5 | 21.5–37.9 |

[a]Normal range, for Ages 13–49, 3.89–6.38 mmol/L; for Ages ≧50 years, 3.89–6.94 mmol/L
[b]Normal range, <6.5% of total hemoglobin
[c]Normal range, 0.26–1.32 nmol/L The patients were monitored throughout the study for fasting plasma glucose levels in their blood (FPG in mmol/L), and for their blood levels of Hemoglobin $A_{1c}$ ($HbA_{1c}$) relative to baseline characteristics. The results of the 26-week trial are presented in Table 2.

TABLE 2

Glucose-Lowering Effect of Rosiglitazone

| | Placebo (n = 158) | RSG 4 mg/day (n = 166) | RSG 8 mg/day (n = 169) |
|---|---|---|---|
| FPG (mmol/L)-Baseline | 12.7 | 12.6 | 12.2 |
| Mean Δ From Baseline (SD) | +1.05 (3.58) | −2.13 (2.91) | −3.00 (2.85) |
| Comparison With Placebo[a] | — | −3.20* | −4.22* |
| 95% CI | — | (−3.94, −2.48) | (−4.95, −3.49) |
| FPG (mg/dL)-Baseline | 228.8 | 226.9 | 219.7 |
| Mean Δ From Baseline (SE) | 8.9 (5.1) | −38.4 (4.1) | −54.0 (3.9) |
| Comparison With Placebo[a] | — | −57.7* | −76* |
| 95% CI | — | (−70.9, −44.6) | (−89.2, −62.9) |
| $HbA_{1c}$ (%)-Baseline | 9.04 | 9.02 | 8.75 |
| Mean Δ From Baseline (SD) | +0.92 (1.21) | −0.28 (1.27) | −0.56 (1.38) |
| Comparison With Placebo[a] | — | −1.21* | −1.54* |
| 95% CI | — | (−1.52, −0.89) | (−1.85, −1.22) | aAdjusted mean difference
*p < 0.0001.

The data presented in Table 2 demonstrate that rosiglitazone at 4 and 8 mg/day has a glucose-lowering effect compared to placebo-treated patients and to baseline. In a further analysis, the change from baseline in $HbA_{1c}$ in a subset of patients who had previously failed to be controlled on dietary therapy alone demonstrated a greater change from baseline in the patients treated with rosiglitazone. These results are shown in Table 3.

TABLE 3

Effect of Rosiglitazone in Diet-Failure Subset

| | Placebo | 4 mg/day | 8 mg/day |
|---|---|---|---|
| $HbA_{1c}$ (%) (Diet-Failure Subset) | | | |
| n= | 45 | 44 | 45 |
| Baseline | 8.5 | 8.75 | 8.51 |
| Mean Δ From Baseline (SD) | 0.47 (1.14) | −0.83 (0.93) | −0.91 (1.04) |

The data in Table 3 establish that rosiglitazone at 4 mg/day caused a 1.3% reduction in $HbA_{1c}$ relative to placebo-treated controls, and at 8 mg/day, caused a 1.38% reduction compared to placebo.

As noted above, rosiglitazone is a preferred glitazone to be combined with a sulfonylurea according to this invention. The sulfonylurea will be employed at a dose of about 0.25 mg to about 500 mg, typically from about 3 mg to about 250 mg. The rosiglitazone will be administered at a dose of about 5 to about 2500 mg per day, and more typically at a dose of about 5 mg to about 50 mg.

Additional examples of combination therapy according to this invention will employ the glitazone BRL 49653 together with a sulfonylurea selected from glyburide, chlorpropamide, tolbutamide, and glipizide. Another combination will be the glitazone TA 174 in combination with a sulfonylurea selected from glisoxepid, acetohexamide, glibornuride, and tolazamide. Still another combination provided by this invention is englitazone together with glibornuride, glyburide, or glisoxepid. Further preferred combinations include pioglitazone with tolbutamide, glipizide, glyburide, or glibornuride.

Several studies have been conducted showing the beneficial effects of pioglitazone, "Pi", ((±)-5-[p-[2-(5-ethyl-2-pyridyl)ethoxy]benzyl]-2,4-thiazolidinedione hydrochloride), both alone and in combination with sulfonylureas, in controlling and promoting hepatic glucose uptake in patients having NIDDM. One such clinical trial used 20 patients having a mean age of 58.2±9.4 (13 males, 7 females). All patients were controlling their blood glucose by diet alone or by taking a sulfonylurea. After establishing each patient's baseline insulin sensitivity, pioglitazone was administered orally at a dose of 30 mg/day, every morning for 3 months. At the end of the 3-month treatment period, fasting plasma glucose (FPG) level significantly ($p<0.01$) decreased from 11.0±1.5 mmol/liter to 8.9±1.1 mmol/liter. Hemoglobin $A_{1c}$ level significantly fell from 9.2±1.8% to 8.3±1.5% ($p<0.01$). Fasting serum insulin and C peptide levels decreased from 83±36 pmol/liter and 0.62±0.21 pmol/liter to 66±29 pmol/liter and 0.58±0.25 nmol/liter, respectively. These results demonstrate that pioglitazone enhances the insulin action in NIDDM patients on diet alone or on concomitant sulfonylurea use, and thereby improves both plasma glucose level and lipid profiles.

In another study, pioglitazone was administered in combination with glipizide (Gl). In a two period cross-over study in 16 normal volunteers, patients received placebo (Pb) plus 5 mg of glipizide, or pioglitazone (45 mg/day) plus 5 mg/day of glipizide. The patients were dosed for 7 days on one treatment, and then for the following 7 days on the alternate treatment. The pharmacokinetic (PK) effects of multiple doses of pioglitazone on steady state glipizide levels was determined. The plasma glipizide PK parameters are shown in Table 4.

TABLE 4

Steady State Glipizine PK Parameters

| PK Parameter | Pb + Gl Mean (SD) | Pi + Gl Mean (SD) |
|---|---|---|
| AUC (0-inf) | 1884 (685) | 1833 (684) |
| Cmax (ng/mL) | 367 (68.4) | 332 (42.0) |
| Tmax (hr) | 2.3 (1.2) | 2.7 (1.2) |
| Kel (l/hr) | 0.214 (0.0524) | 0.222 (0.0516) |
| Tl/2 el (hr) | 3.51 (1.33) | 3.39 (1.31) |
| Cl/F (Uhr) | 2.85 (0.624) | 2.94 (0.679) |
| Vd/F(L) | 13.5 (1.60) | 13.4 (1.55) |

The PK and statistical analyses of the data indicate that the coadministration of Pi did not alter the disposition or steady-state PK characteristics of Gl. No serious adverse events and no clinically significant trends in vital signs, physical findings, or clinical laboratory tests were observed.

In another study in patients, pioglitazone alone, and together with sulfonylureas, significantly increased hepatic glucose uptake (HGU). Thirty patients were selected for the trial. Four controlled their blood glucose on diet alone; the remaining 26 were taking a sulfonylurea. Twenty-one patients were given 30 mg of pioglitazone daily for 12 weeks. Nine patients (one on diet alone, 8 on sulfonylurea drugs), were given placebo. The group receiving pioglitazone showed an increase in HGU from 28.5±19.4 to 59.4±27.1, a 12% increase in hepatic glucose uptake. The group receiving placebo showed no significant change in hepatic glucose uptake.

Figure 2:
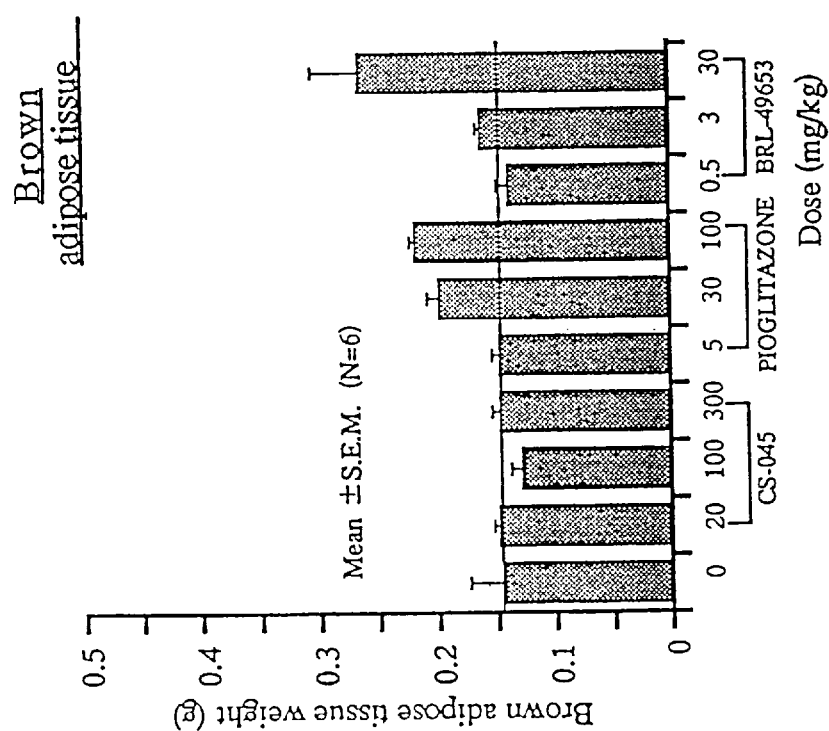
FIG. 2 Dose response of troglitazone, pioglitazone, and rosiglitazone in increases in brown adipose tissue in rats.
Figure 3:
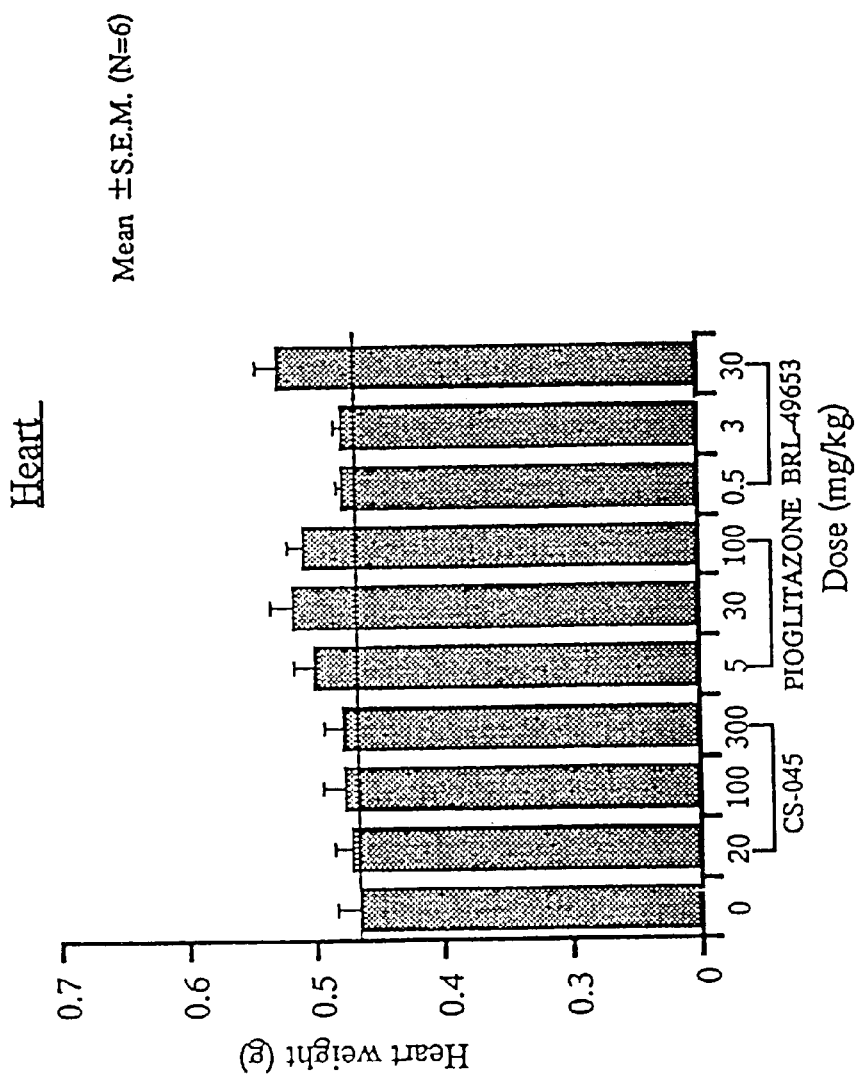
FIG. 3 Dose response of troglitazone, pioglitazone, and rosiglitazone in increasing heart weight (mass) in rats.
Figure 4:
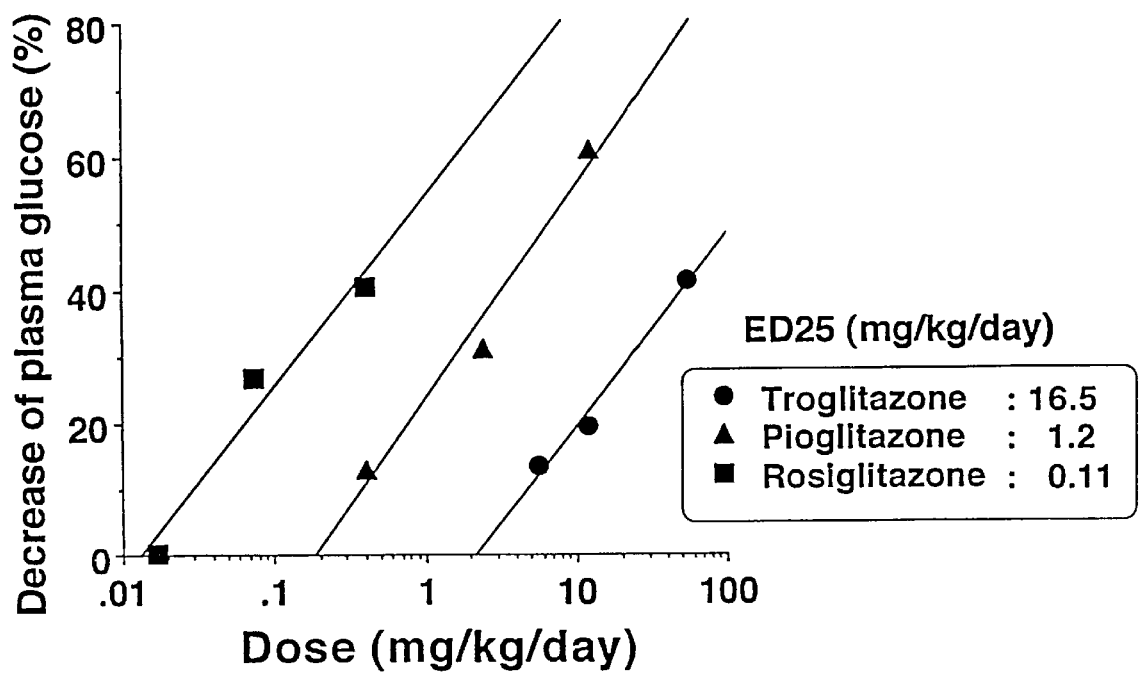
FIG. 4 Dose response ($ED_{25}$) of troglitazone, pioglitazone, and rosiglitazone in causing a decrease in plasma glucose in KK mice.
Figure 5:
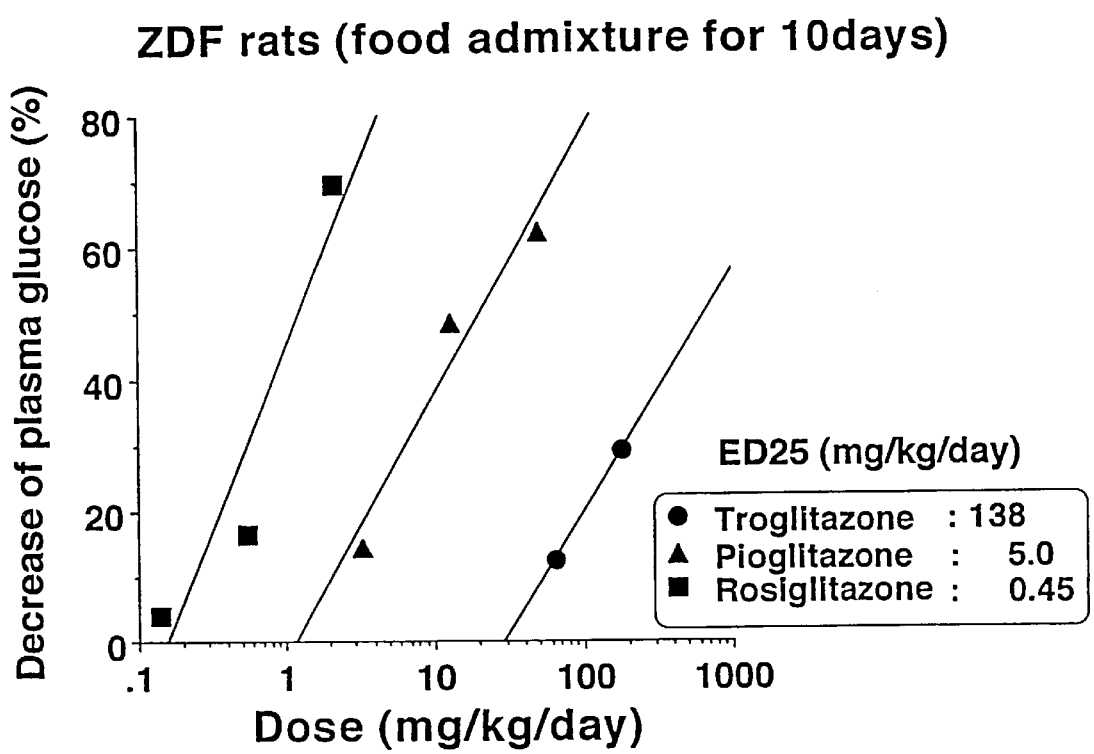
FIG. 5 Dose response ($ED_{25}$) of troglitazone, pioglitazone, and rosiglitazone in decreasing plasma glucose (%) in ZDF rats.
Figure 6:
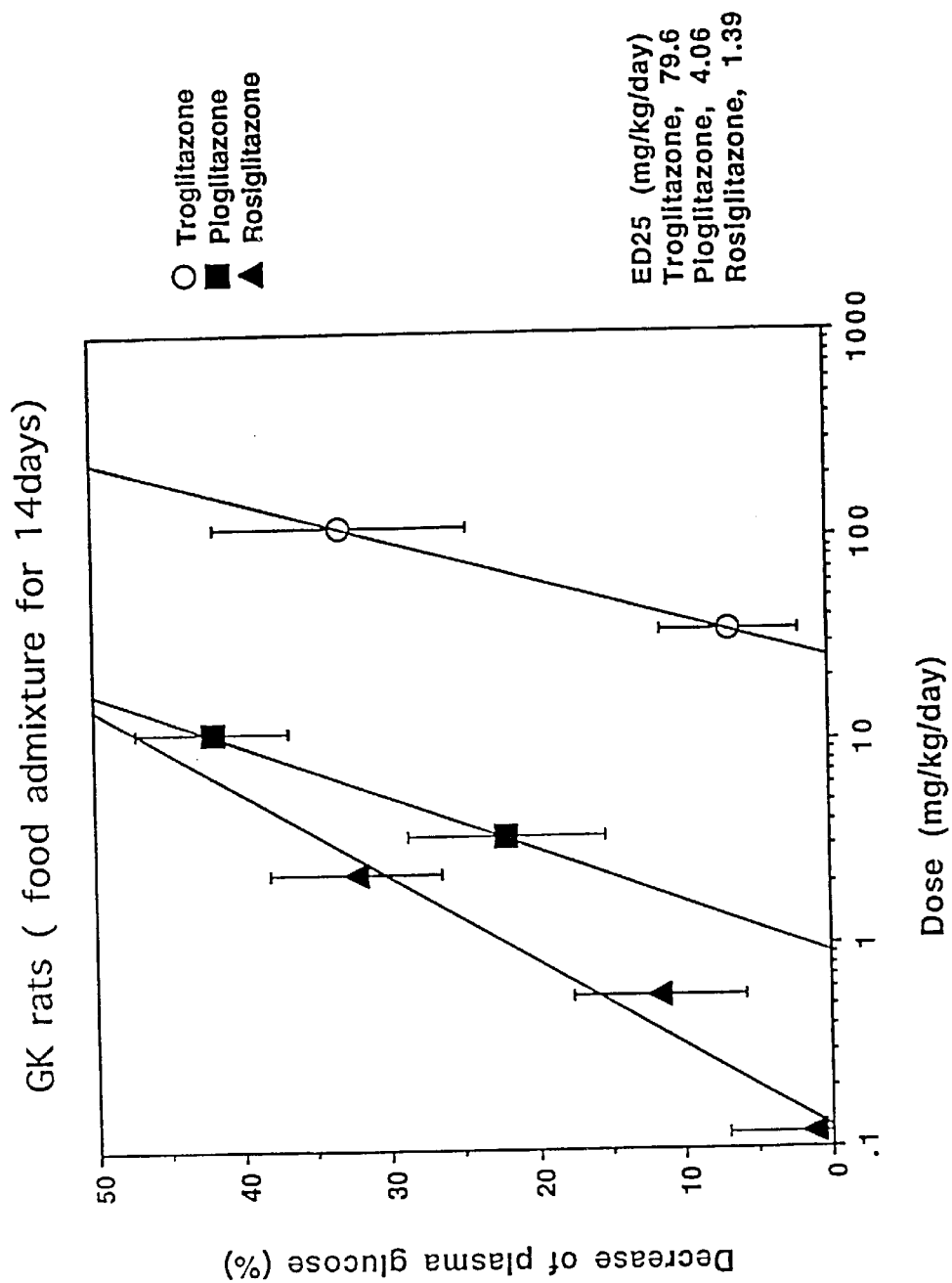
FIG. 6 Dose response of troglitazone, pioglitazone, and rosiglitazone in decreasing plasma glucose (%) in GK rats.
Figure 7:
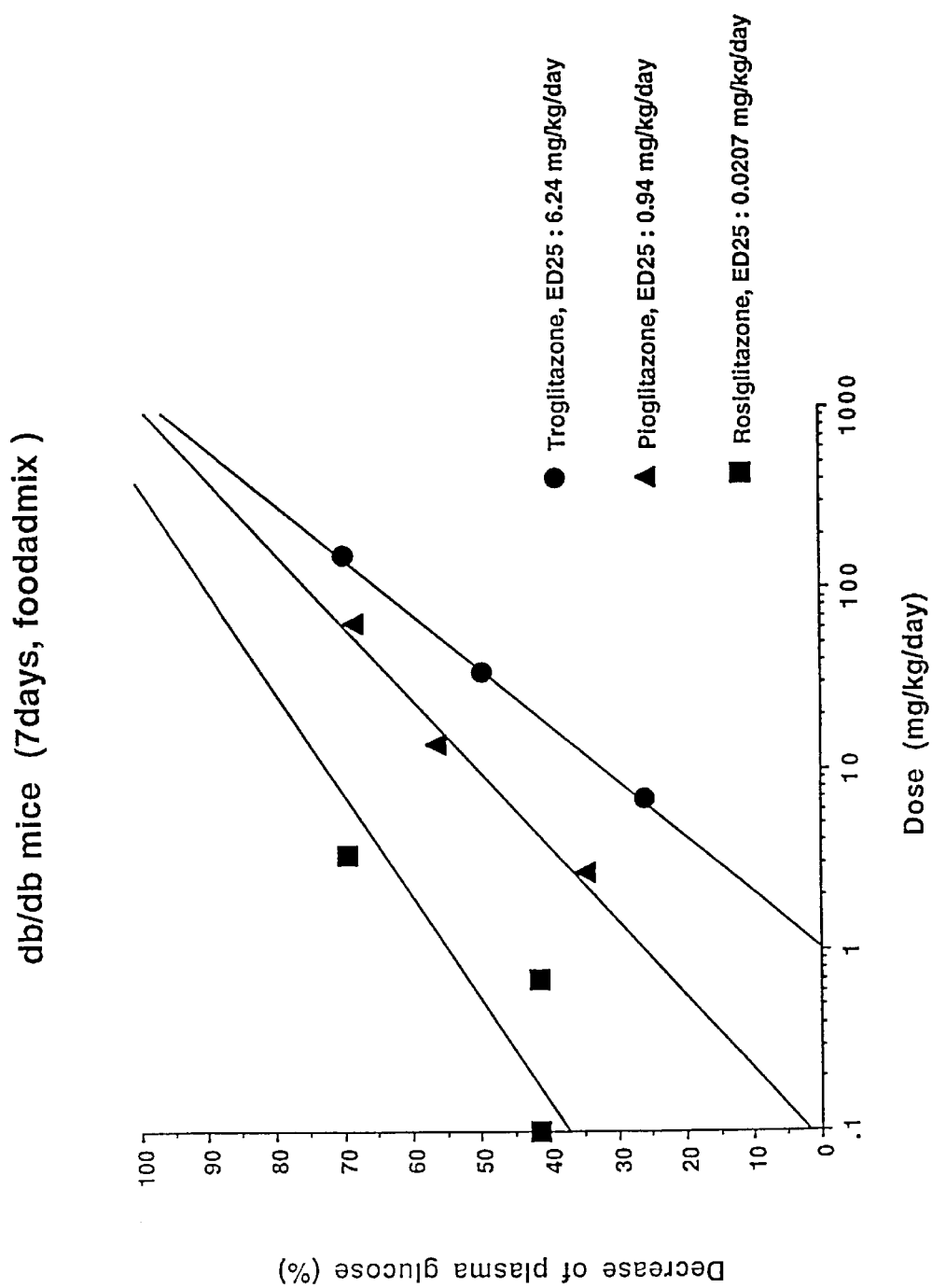
FIG. 7 Dose response of troglitazone, pioglitazone, and rosiglitazone in decreasing plasma glucose (%) in db/db mice.

As noted above, the glitazones are a class of thiazolidinediones which have been shown to enhance hepatic and peripheral glucose uptake in animals, including humans, and are thus useful for treating diabetes mellitus. All of the glitazone compounds operate by the same mechanism within an animal system. Several studies have established the close similarity in biological activity of various glitazones from within the thiazolidinedione class. For example, troglitazone, pioglitazone, and rosiglitazone all cause a slight reduction in red blood cell counts when administered at various dosages to female rats (FIG. 1). Similarly, all three glitazones have about the same negligible effect on brown adipose tissue weight changes in rats (FIG. 2). Pioglitazone causes a slight increase in heart weight, whereas troglitazone has essentially no affect, and rosiglitazone causes an increase only at higher dose levels (FIG. 3). When tested in various mouse models, all three glitazones caused a substantial decrease in plasma glucose levels in a dose dependent fashion (FIGS. 4, 5, 6, and 7).

The foregoing studies establish that the glitazones are a class of antidiabetic agents which exert a very similar spectrum of biological effects in animals. The studies also establish the ability of the glitazones to be used in combination with a sulfonylurea for the significant increase in hepatic glucose uptake, and the dramatic reduction in plasma glucose levels. The combinations are thus particularly well suited to the treatment of type 2 diabetes, and can be utilized in the treatment of impaired glucose tolerance in order to even prevent or delay the onset of NIDDM.

The glitazones can also be utilized in combination with a biguanide such as metformin, as well as in combination with a biguanide plus a sulfonylurea. Several clinical trials have established the unexpected biological efficacy that is achieved with a combination of troglitazone and metformin, as well as troglitazone, metformin, and glyburide.

In one clinical trial, patients were treated with monotherapy of metformin or troglitazone for 3 months, followed by combination therapy for 3 months. Twenty-nine patients diagnosed as having NIDDM were randomized. Fifteen subjects received metformin monotherapy, 1000 mg orally twice a day for 3 months. A group of 14 subjects were dosed orally with 400 mg of troglitazone once daily for 3 months. One patient randomized to troglitazone terminated participation after 2 weeks. One patient from each group completed the 3-month monotherapy phase, but withdrew prior to initiation of combination therapy. Two additional subjects, initially in the troglitazone monotherapy group, later withdrew from the combination phase before completion. The baseline characteristics of all subjects following the 3-month monotherapy phase are given in Table 5 below.

TABLE 5

Baseline Characteristics of Subjects Who Completed
the 3-Month Monotherapy Phase of the Trial

|  | Metformin Group (n = 15) | Troglitazone Group (n = 13) | p = |
|---|---|---|---|
| Age (years) | 51 (±3) | 53 (±2) | 0.32 (NS) |
| Weight (kg) | 99 (±4) | 96 (±7) | 0.68 (NS) |
| BMI (kg/m$^2$) | 33.7 (±1.8) | 34.0 (±2.3) | 0.94 (NS) |
| FPG (after "wash-out") | 287 (±22) | 275 (±21) | 0.71 (NS) |
| HbA$_{1c}$ (at screening) | 9.8 (±0.5) | 9.3 (±0.5) | 0.42 (NS) |
| Fasting insulin | 24 (±3) | 35 (±7) | 0.16 (NS) |
| Fasting C-peptide | 1.9 (±0.1) | 2.3 (±0.2) | 0.13 (NS) |

The patients were evenly matched for age, body mass index (BMI), fasting plasma glucose (FPG), HbA$_{1c}$, and fasting insulin and C-peptide. The treatment group was in general obese, moderately diabetic, and had a mean BMI of 33.5 kg/m$^2$, a mean HbA$_{1c}$ (prior to starting the study) of 9.6%, and a mean FPG of 280 mg/dL.

After the initial 3-month period of monotherapy, the remaining subjects were dosed with a combination of metformin and troglitazone (1000 mg metformin BID, 400 mg troglitazone QD) for an additional 3-month period.

Figure 8:
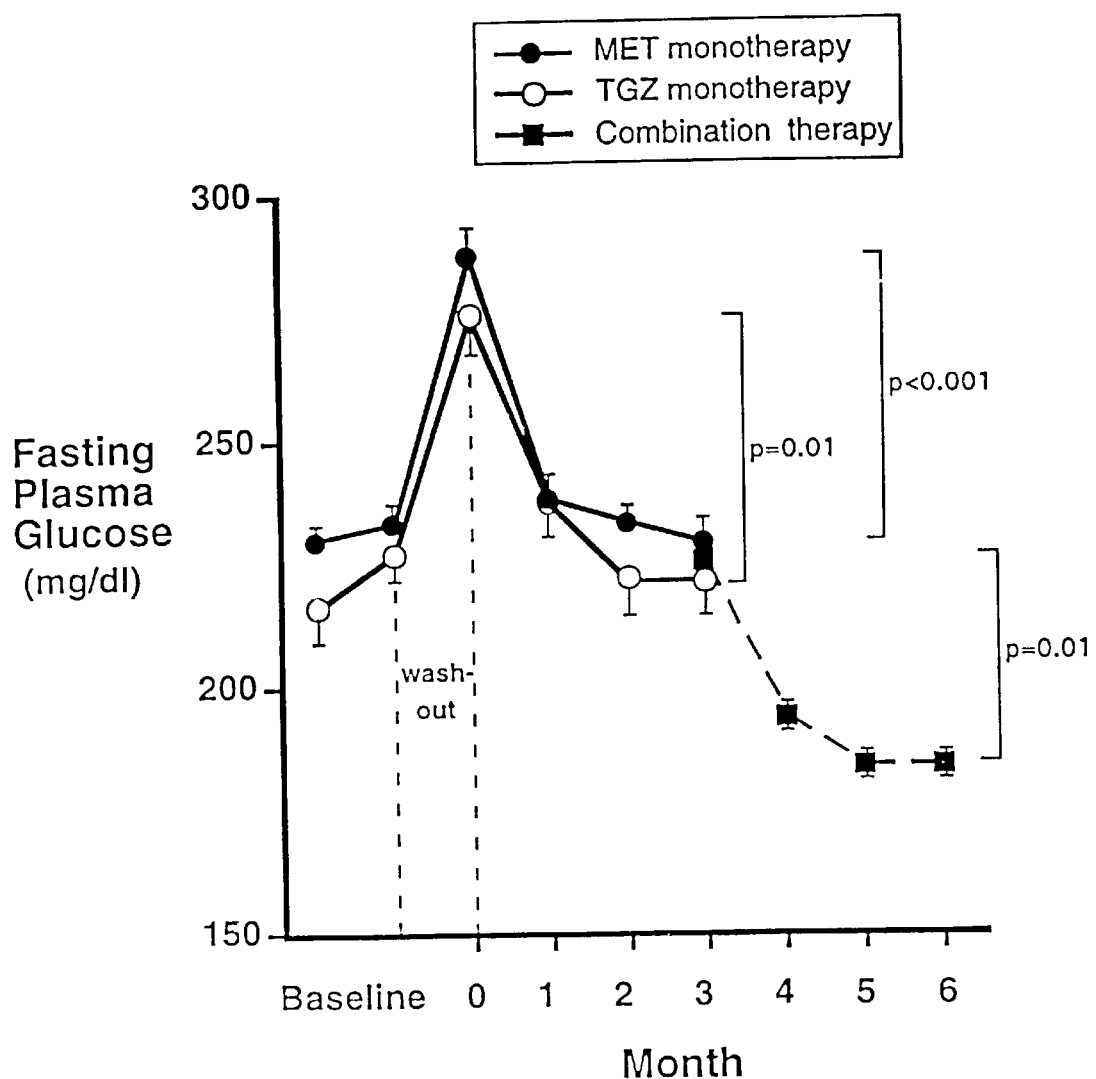
FIG. 8 Change in fasting plasma glucose (FPG) (±SEM) during metformin and troglitazone monotherapy and during metformin and troglitazone combination therapy.
Figure 9:
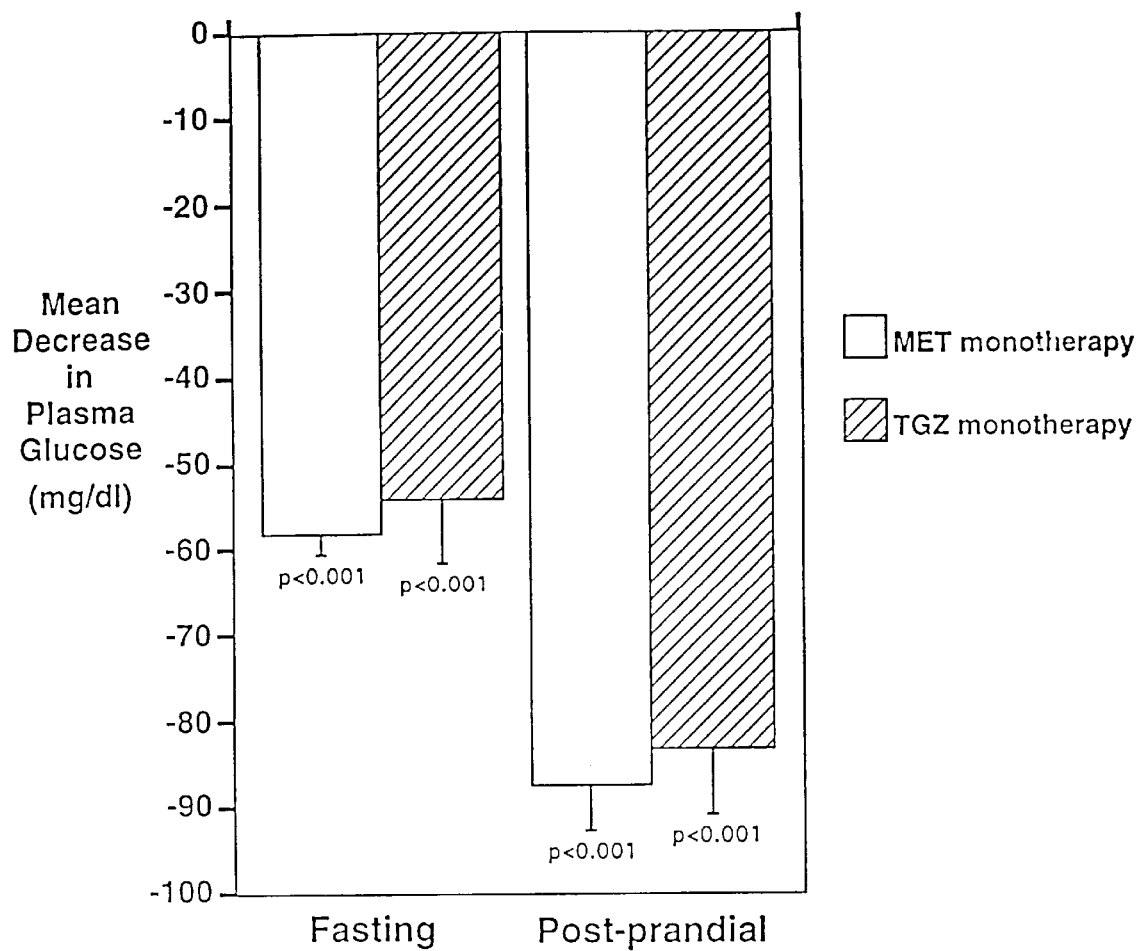
FIG. 9 Changes in FPG and post-prandial glucose (PPG (±SEM) at 3 months of monotherapy of metformin and of troglitazone.
Figure 10:
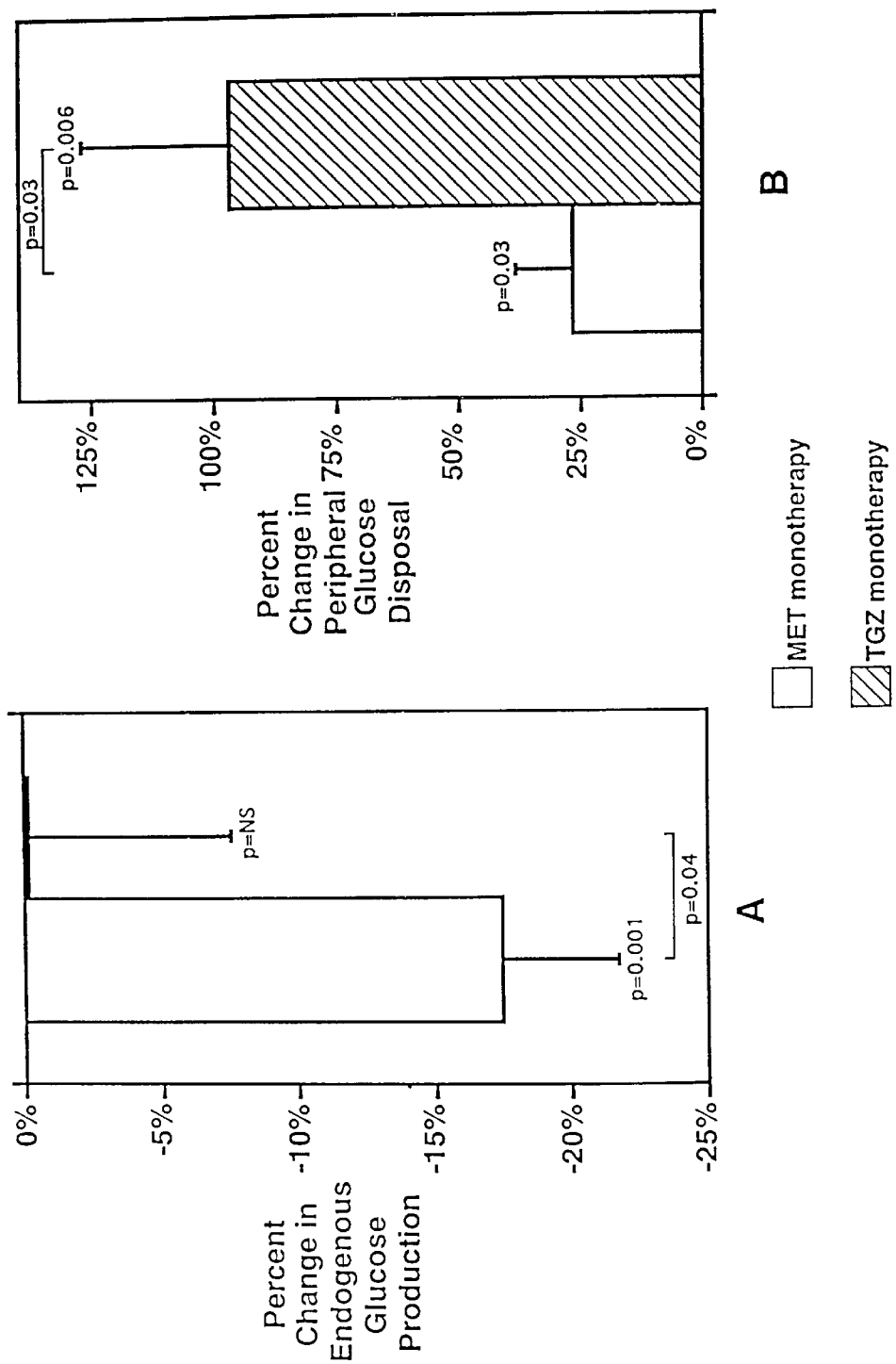
FIG. 10 (A) Mean percent change in endogenous glucose production (EGP) after 3 months of monotherapy of metformin and of troglitazone. (B) Mean percent change in glucose disposal rates (GDR) under hyperinsulinemic clamp conditions after 3 months of monotherapy of metformin and of troglitazone.

At 3 months on monotherapy, both metformin and troglitazone caused a 20% decrease from baseline of FPG; 58 mg/dL and 54 mgldL, respectively (FIG. 8). HbA$_{1c}$ levels did not change significantly with either drug. Mean postprandial glucose decreased about 25% for both groups (metformin 87 mg/dL, troglitazone 83 mg/dL), as shown in FIG. 9. Post-prandial circulating insulin and C-peptide decreases were insignificantly different from baseline for both treatment groups. Following a 12-hour fasting period, all subjects were given a hyperinsulinemic-englycemic clamp assay. After the 3-month monotherapy treatment, EGP decreased from 108 to 87 mg/m$^2$/min (18%) in the metformintreated group (FIG. 10A), while troglitazone had no effect on EGP (FIG. 10B). In contrast, metformin caused less than 27% increase in glucose disposal rate (GDP) (240 to 272 mg/m$^2$/min) (FIG. 10B), whereas troglitazone caused a 97% increase (172 to 265 mg/m$^2$/min) (FIG. 10B).

Figure 11:
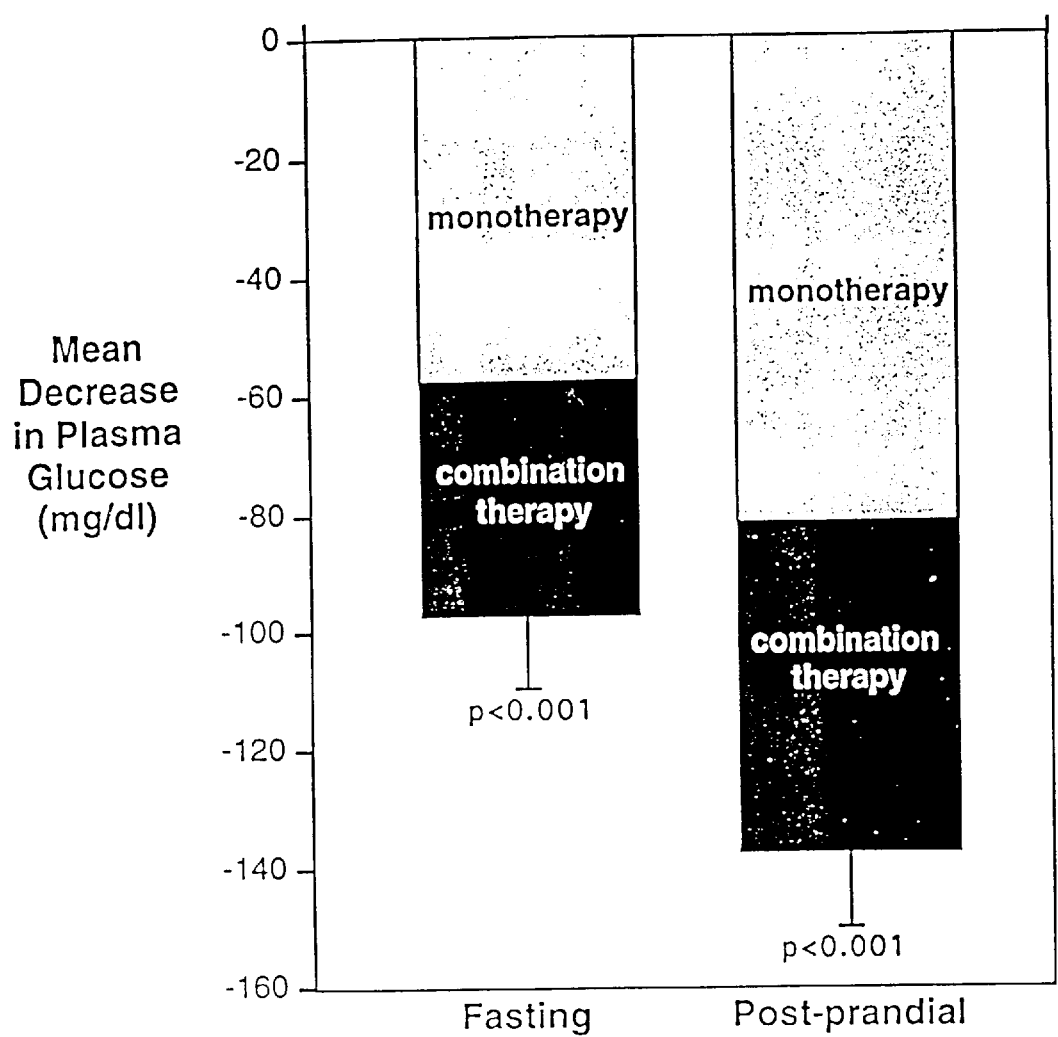
FIG. 11 Changes in FPG and PPG after 3 months monotherapy of metformin and of troglitazone, and after an additional 3 months of combination therapy (metformin and troglitazone).
Figure 12:
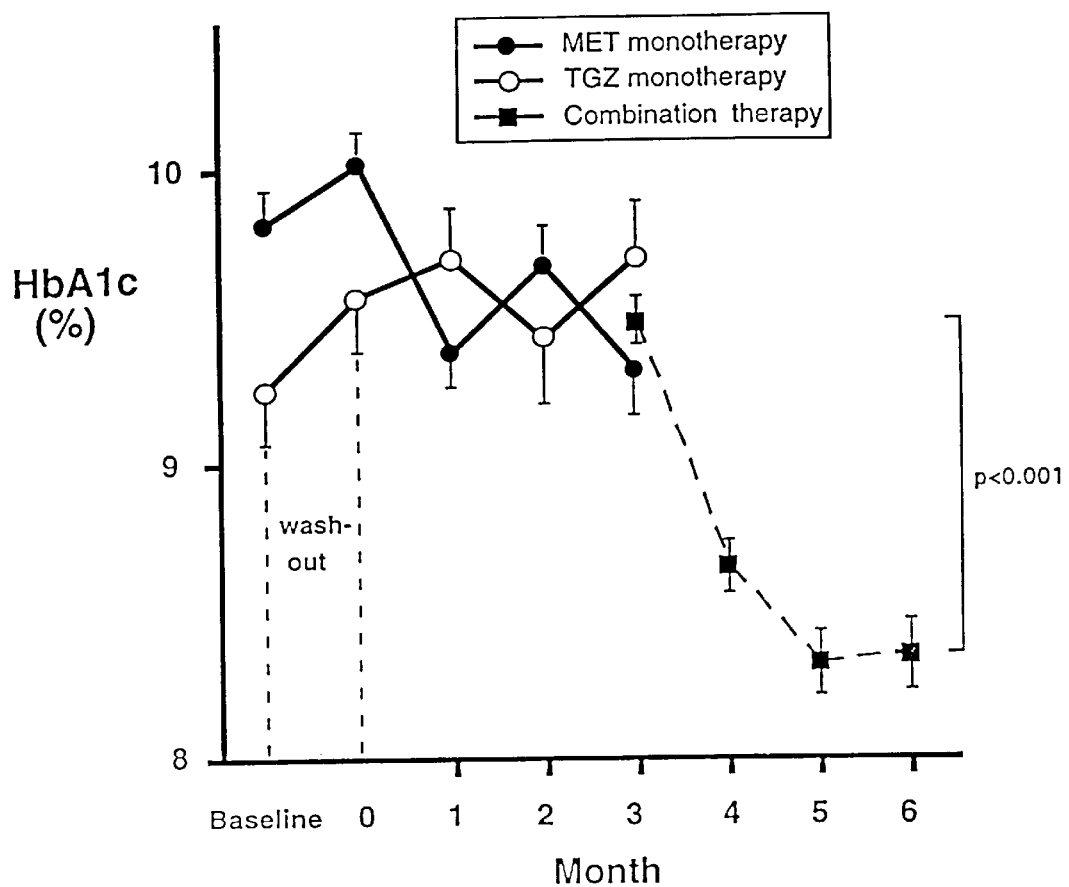
FIG. 12 Change in hemoglobin A1c ($HbA_{1c}$) (±SEM) during 3 months of monotherapy of metformin and troglitazone and after an additional 3 months of combination therapy (metformin and troglitazone).

When the study patients were given the combination of metformin and troglitazone for 3 months, dramatic and unexpected effects were observed. Fasting plasma glucose levels decreased an additional 18% (41 mg/dL) as shown in FIG. 8. Compared to baseline values, the mean decrease in FPG in all subjects over the entire 6-month treatment period was 98 mg/dL, or 35%. During the meal tolerance test, combination therapy caused an additional 21% decrease in plasma glucose (PG), or 54 mg/dL (FIG. 11). During the entire 6-month treatment period, total PG fell 41% or 140 mg/dL. HbA$_{1c}$ levels decreased 1.2% during the combination therapy (FIG. 12).

The foregoing study establishes that the combination of metformin and troglitazone causes a clinically significant and unexpected further lowering of both fasting and postprandial glucose compared to either agent used alone. The combination provided by this invention thus provides further improvement in glucose control, without stimulation of insulin secretion.

Even more surprising are the clinical results observed when using a three-way combination of biguanide, sulfonylurea, and glitazone. A clinical trial was carried out assessing the effects of metformin, glyburide, and troglitazone when compared to a typical treatment regimen of glyburide and metformin. Two hundred NIDDM patients were enrolled in a double-blind, randomized, placebo-controlled multicenter study. All enrolled patients had compromised glycemic control and were currently treated with a sulfonylurea (comparable in dosage to at least 20 mg of glyburide) and at least 1500 mg of metformin daily. Of the 200 patients enrolled, 178 completed the 24-week trial. The study population consisted of 57% males, 43% females, with median age of 59. Patients had an average duration of NIDDM of 11.3 years. The population had an average weight of 85 kg (187 lbs), and BMI of 30.1 kg/m$^2$. At the start of the trial, 101 patients received oral dosing of troglitazone (400 mg once daily), a sulfonylurea (SU), and metformin. The control group of 99 subjects received a sulfonylurea and metformin. The primary efficacy parameter measured was HbA$_{1c}$. Secondary efficacy parameters were FSG, C-peptide, serum total insulin, BMI weight, triglycerides, total cholesterol (TC), high-density lipoprotein (HDL), and low-density lipoprotein (LDL). Baseline glycemic levels at the start of the trial were: HbA$_{1c}$: 9.7%; FPG: 234 mg/dL; circulating insulin level: 14.4 µIN/mL; C-peptide: 3.4 ng/mL. The results of the clinical study after 24 weeks of treatment are presented in Table 6.

TABLE 6

Changes From Baseline at 24 Weeks

|  | SU + Metformin | SU + Metformin + Troglitazone | Adjusted Difference |
|---|---|---|---|
| HbA$_{1c}$ | +0.1 | −1.3 (p < 0.001) | −1.4 |
| FPG | +6 | −42 (p < 0.001) | −48 |
| Circulating Insulin | +1.4 | −2.8 (p < 0.001) | −3.3 |
| C-peptide | 0 | −0.2 (p = 0.16) | −0.2 |
| Triglycerides | +43 | −36 (p = 0.07) | −67 |
| Total Colesterol | +6 | +8 (p = 0.05) | 4.8 |
| HDL | +1 | +4 (p = 0.01) | 3 |
| LDL | +2 | +11 (p = 0.002) | 9 |

In the foregoing study, plasma glucose levels were reduced by 42 mg/dL at Week 8 in the group receiving the triple combination. This is a dramatically rapid reduction in FPG, showing the unexpectedly fast onset of action achieved with the triple combination, and the synergy associated with metformin, sulfonylurea, and glitazone. This represents good glycemic control in about one-half the time period normally observed in clinical settings using antidiabetic agents in monotherapy, or even using a combination of sulfonylurea and biguanide. Equally surprising was the dramatic reduction in endogenous insulin (19%) caused by the triple combination. Moreover, while the sulfonylurea/metformin combination had no effect on C-peptide levels, the triple combination of sulfonylurea/biguanide/glitazone caused a 7% reduction. Similarly, while the sulfonylurea/metformin treated group had an increase in triglycerides of 43 mg/dL, the sulfonylurea/glitazoneibiguanide combination caused a reduction of 36 mg/dL.

The foregoing clinical trial establishes that three-way combinations of sulfonylurea/biguanide/glitazone are surprisingly effective at reducing HbA$_{1c}$, and cause a very rapid and significant reduction in plasma glucose levels. Such combinations are especially well-suited to rapidly bringing under control a patient suffering from NIDDM and having dangerously high levels of plasma glucose. Another important and significant aspect of the foregoing clinical trial is the fact that the patients experienced very few adverse events, and the dropout rate was extremely low.

What is claimed is:

1. A composition comprising from about 3 mg to about 250 mg of a sulfonylurea antidiabetic agent, from about 5 mg to about 2500 mg of a glitazone antidiabetic agent selected from troglitazone, rosiglitazone and pioglitazone, and from about 300 mg to about 2000 mg of a biguanide antidiabetic agent, said amounts being synergistic in the treatment of non-insulin dependent diabetes mellitus.

2. A composition of claim 1 wherein the sulfonylurea is selected from glisoxepid, glyburide, acetohexamide, chlorpropamide, glibornuride, tolbutamide, tolazamide, glipizide, gliclazide, gliquidone, glyhexamide, phenbutamide, and tolcyclamide.

3. A composition of claim 1 wherein the biguanide is metformin.

4. A synergistic composition comprising from about 100 mg to about 1000 mg of troglitazone, from about 3 mg to about 250 mg of glyburide, and from about 300 mg to about 2000 mg of metformin.

5. A synergistic composition comprising from about 5 mg to about 10 mg of rosiglitazone, from about 3 mg to about 250 mg of a sulfonylurea, and from about 300 mg to about 2000 mg of metformin.

6. A synergistic composition comprising from about 50 mg to about 200 mg of pioglitazone, from about 3 mg to about 250 mg of a sulfonylurea, and from about 300 mg to about 2000 mg of metformin.

7. A method of treating diabetes by administering to a patent in need of treatment from about 3 mg to about 250 mg of a sulfonylurea antidiabetic agent in combination with from about 5 mg to about 2500 mg of a glitazone antidiabetic agent selected from troglitazone, rosiglitazone and pioglitazone and from about 300 mg to about 2000 mg of a biguanide antidiabetic agent, wherein said amounts are synergistic for the treatment of non-insulin dependent diabetes mellitus.

8. A method according to claim 7 wherein the sulfonylurea antidiabetic agent is selected from glisoxepid, glyburide, acetohexamide, chlorpropamide, glibornuride, tolbutamide, tolazamide, glipizide, gliclazide, gliquidone, glyhexamide, phenbentamide, and tolcyclamide.

9. A method according to claim 8 wherein the glitazone antidiabetic agent is selected from troglitazone, pioglitazone, and rosiglitazone.

10. A method according to claim 8 wherein the biguanide is metformin.

11. A method according to claim 10 wherein the glitazone is troglitazone.

12. A method according to claim 10 wherein the glitazone is rosiglitazone.

13. A method according to claim 10 wherein the glitazone is pioglitazone.

14. A method of treating diabetes by administering to a patient in need of treatment from about 5 mg to about 10 mg of rosiglitazone together with from about 300 mg to about 2000 mg of metformin and from about 3 mg to about 250 mg of a sulfonylurea, wherein said amounts are synergistic for the treatment of non-insulin dependent diabetes mellitus.

15. A method of treating diabetes by administering to a patient in need of treatment from about 100 mg to about 1000 mg of troglitazone together with from about 300 mg to about 2000 mg of metformin and from about 3 mg to about 250 mg of a sulfonylurea, wherein said amounts are synergistic for the treatment of non-insulin dependent diabetes mellitus.

16. A method of treating diabetes by administering to a patient in need of treatment from about 50 mg to about 200 mg of pioglitazone together with from about 300 mg to about 2000 mg of metformin and from about 3 mg to about 250 mg of a sulfonylurea, wherein said amounts are synergistic for the treatment of non-insulin dependent diabetes mellitus.

* * * * *